United States Patent
Shahriar et al.

(10) Patent No.: US 12,064,216 B2
(45) Date of Patent: Aug. 20, 2024

(54) SYNCHRONIZATION OF PHYSIOLOGICAL DATA

(71) Applicant: Nokia Technologies Oy, Espoo (FI)

(72) Inventors: Muneem Shahriar, Sunnyvale, CA (US); Durgaprasad Shamain, San Jose, CA (US)

(73) Assignee: Nokia Technologies Oy, Espoo (FI)

( * ) Notice: Subject to any disclaimer, the term of this patent is extended or adjusted under 35 U.S.C. 154(b) by 77 days.

(21) Appl. No.: 16/958,525

(22) PCT Filed: Nov. 16, 2018

(86) PCT No.: PCT/EP2018/081541
§ 371 (c)(1),
(2) Date: Jun. 26, 2020

(87) PCT Pub. No.: WO2019/129418
PCT Pub. Date: Jul. 4, 2019

(65) Prior Publication Data
US 2021/0052166 A1    Feb. 25, 2021

(30) Foreign Application Priority Data
Dec. 29, 2017   (EP) .................................... 17211016

(51) Int. Cl.
*A61B 5/0205*    (2006.01)
*A61B 5/00*    (2006.01)
(Continued)

(52) U.S. Cl.
CPC .............. *A61B 5/0205* (2013.01); *A61B 5/30* (2021.01); *A61B 5/369* (2021.01); *A61B 5/024* (2013.01); *A61B 5/08* (2013.01)

(58) Field of Classification Search
CPC ......... A61B 5/0205; A61B 5/024; A61B 5/08; A61B 5/24; A61B 5/30; A61B 5/352; A61B 5/369; A61B 5/7289
See application file for complete search history.

(56) References Cited

U.S. PATENT DOCUMENTS

2003/0036685 A1    2/2003   Goodman ..................... 600/300
2003/0208129 A1*  11/2003  Beker ..................... A61B 5/366
                                                             600/509

(Continued)

FOREIGN PATENT DOCUMENTS

DE    102016203338 A1    9/2017
JP    2010093361 A       4/2010

(Continued)

OTHER PUBLICATIONS

Srinivasan et al., "Heart rate calculation from ensemble brain wave using wavelet and Teager-Kaiser energy operator", Nov. 5, 2015, IEEE Conference, p. 5924-5927 (Year: 2015).*

(Continued)

*Primary Examiner* — Jonathan T Kuo
*Assistant Examiner* — Vynn V Huh
(74) *Attorney, Agent, or Firm* — Harrington & Smith

(57) ABSTRACT

Methods, systems, and computer-readable media for synchronizing physiological signals collected from two or more physiological sensors are provided. Examples of physiological signals may include respiration, heartbeat, electroencephalogram, and gastrointestinal signals. A method, an apparatus, and a computer program for synchronizing two or more physiological signals may involve collecting first data from a first sensor and second data from a second sensor, each of the first data and the second data represents a plurality of physiological signal components; extracting a common physiological signal component of the first data and the second data; correlating the common physiological (Continued)

signal component of the plurality of physiological signal components of the first data and of the plurality of physiological signal components of the second data; and based on the correlating, synchronizing a first physiological signal component included in the first data and a second physiological signal component included in the second data.

20 Claims, 6 Drawing Sheets

(51) Int. Cl.
| | |
|---|---|
| *A61B 5/024* | (2006.01) |
| *A61B 5/08* | (2006.01) |
| *A61B 5/24* | (2021.01) |
| *A61B 5/30* | (2021.01) |
| *A61B 5/352* | (2021.01) |
| *A61B 5/369* | (2021.01) |

(56) References Cited

U.S. PATENT DOCUMENTS

| | | | |
|---|---|---|---|
| 2004/0167418 A1* | 8/2004 | Nguyen | G16H 40/63 |
| | | | 600/513 |
| 2005/0113672 A1 | 5/2005 | Salla et al. | |
| 2009/0082692 A1 | 3/2009 | Hale et al. | |
| 2011/0125060 A1* | 5/2011 | Telfort | A61B 7/003 |
| | | | 600/586 |
| 2011/0209704 A1 | 9/2011 | Jafari et al. | |
| 2011/0224602 A1 | 9/2011 | Struijk et al. | |
| 2013/0046190 A1 | 2/2013 | Davies | |
| 2014/0275889 A1* | 9/2014 | Addison | A61B 5/14551 |
| | | | 600/324 |
| 2015/0134261 A1 | 5/2015 | O'Connor et al. | |
| 2016/0151022 A1* | 6/2016 | Berlin | A61B 5/7246 |
| | | | 600/301 |
| 2016/0228022 A1 | 8/2016 | Hayashi et al. | |
| 2019/0261881 A1* | 8/2019 | Iasemidis | A61B 5/316 |

FOREIGN PATENT DOCUMENTS

| | | | |
|---|---|---|---|
| JP | 2011191142 A | 9/2011 | |
| WO | 03/096894 A1 | 11/2003 | |
| WO | 2012/042437 A2 | 4/2012 | |
| WO | 2015/196298 A1 | 12/2015 | |
| WO | WO-2017007098 A2 | 1/2017 | |
| WO | 2017/136352 A1 | 8/2017 | |
| WO | WO-2017136352 A1 * | 8/2017 | A61B 5/0002 |
| WO | WO-2017158273 A1 | 9/2017 | |

OTHER PUBLICATIONS

Nakamura et al., "Collaborative Processing of Wearable and Ambient Sensor System for Blood Pressure Monitoring", Sensors, vol. 11, No. 7, 2011, pp. 6760-6770.

Extended European Search Report received for corresponding European Patent Application No. 17211016.5, dated Jul. 3, 2018, 7 pages.

Devuyst et al., "Removal of ECG Artifacts from EEG using a Modified Independent Component Analysis Approach", 30th Annual International Conference of the IEEE Engineering in Medicine and Biology Society, Aug. 20-24, 2008, pp. 5204-5207.

Hironaga et al., "Localization of Individual Area Neuronal Activity", NeuroImage, vol. 34, No. 4, Feb. 15, 2007, pp. 1519-1534.

International Search Report and Written Opinion received for corresponding Patent Cooperation Treaty Application No. PCT/EP2018/081541, dated Feb. 27, 2019, 15 pages.

* cited by examiner

SYNCHRONIZATION OF PHYSIOLOGICAL DATA

RELATED APPLICATION

This application claims priority to PCT Application No. PCT/EP2018/081541, filed on Nov. 16, 2018, which claims priority to European Application No. 17211016.5, filed on Dec. 29, 2017, each of which is incorporated herein by reference in its entirety.

BACKGROUND

In some applications, physiological signals are collected from two or more sensors. The process of aligning these signals with respect to one another is called synchronization. Synchronization of physiological data collected by different sensors is important because it ensures the accuracy of processing for applications that use or require physiological signals from different sensors.

Processing physiological signals from different sensors may be challenging to achieve properly due to differences in the sensitivity, response time, communication channel latencies, etc. of each sensor. Attaching timestamps or other information or signal generated for the purpose of synchronizing physiological signals requires additional devices and/or resources. In some applications, generating a signal for synchronizing physiological signals is not feasible. For example, a generated signal may interfere with a physiological signal or with the proper functioning of a medical device (e.g., a pace maker).

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Features of the disclosure relate to systems, apparatuses, computer-implemented methods, and computer-readable media for synchronizing physiological signals from multiple sensors.

A technique for synchronizing two or more physiological signals discussed herein may depend on a common-mode signal embedded within each collected signal in lieu of timestamps. This common-mode signal may be at a higher frequency (e.g., "fast-moving") compared to other components of the measured signals (e.g., "slow-moving").

The fast-moving signal may be linked to exactly one physiological process (e.g., heart beating, respiration, etc.) and, therefore, by design, non-stationary (i.e., time varying in its statistical signal properties). Moreover, the fast-moving signal may be inconspicuously embedded (i.e., low strength) in the slow-moving signal, and may not be discernible until context-based filtering is applied.

In accordance with one or more examples, an apparatus may comprise hardware or any means for collecting first data from a first sensor and second data from a second sensor. Each of the first data and the second data may represent a plurality of physiological signal components. The apparatus may further comprise means for extracting a common physiological signal component of the first data and the second data and correlating the common physiological signal component of the plurality of physiological signal components of the first data and of the plurality of physiological signal components of the second data. In addition, the apparatus may comprise means for synchronizing a first physiological signal component included in the first data and a second physiological signal component included in the second data based on the correlating.

In some embodiments, extracting the common physiological signal component may comprise filtering the first data and the second data to isolate a common high frequency component of the first data and second data.

In some embodiments, the first sensor and the second sensor may be configured to collect at least respiration signals. In further embodiments, the first sensor and the second sensor may be configured to collect at least electroencephalogram (EEG) signals.

In some embodiments, the correlating may comprise cross-correlating the physiological signals of the first data and the physiological signals of the second data. Moreover, the common physiological signal component of the first data and the second data may correspond to a heartbeat signal. In some embodiments, the common physiological signal component of the first data and the second data may correspond to at least one of gamma brain waves, beta brain waves, alpha brain waves, and theta brain waves.

In some embodiments, at least one of the first sensor and the second sensor may be configured to detect at least gastrointestinal muscle movement signals. In some embodiments, the first sensor and the second sensor may be configured to detect signals of different types.

In some embodiments, the means may comprise at least one processor and at least one memory including computer program code. The at least one memory and computer program code may be configured to, with the at least one processor, cause the performance of the apparatus.

In accordance with one or more examples, a method may comprise collecting first data from a first sensor and second data from a second sensor. Each of the first data and the second data may represent a plurality of physiological signal components. The method may further comprise extracting a common physiological signal component of the first data and the second data and correlating the common physiological signal component of the plurality of physiological signal components of the first data and of the plurality of physiological signal components of the second data. In some embodiments, the method may comprise synchronizing a first physiological signal component included in the first data and a second physiological signal component included in the second data based on the correlating. In some embodiments, the common physiological signal component of the first data and the second data may correspond to a heartbeat signal.

Any of the example methods can be implemented as executable instructions or computer programs, which may be stored in computer readable media.

Other features and advantages of the disclosure will be apparent from the additional description provided herein.

BRIEF DESCRIPTION OF THE DRAWINGS

A more complete understanding of the present disclosure and the advantages thereof may be acquired by referring to the following description in consideration of the accompanying drawings, in which like reference numbers indicate like features, and wherein.

DETAILED DESCRIPTION

In the following description, reference is made to the accompanying drawings, which show various features of the examples described herein. It is to be understood that additional examples are within the scope of the disclosure.

As will be appreciated by one of skill in the art upon reading the following disclosure, various features described herein may be embodied as a method, an apparatus, a computer system, a computer program, and/or a computer program product. Accordingly, those features may take the form of an entirely hardware embodiment, an entirely software embodiment or an embodiment combining software and hardware aspects. Furthermore, such features may take the form of a computer program product stored by one or more computer-readable storage media having computer-readable program code, or instructions, stored in or on the storage media. Any suitable computer readable storage media may be utilized, including non-transitory media, such as hard disks, CD-ROMs, optical storage devices, magnetic storage devices, and/or any combination thereof. In addition, various signals representing data or events as described herein may be transferred between a source and a destination in the form of electromagnetic waves traveling through transitory or signal-conducting media such as metal wires, optical fibers, and/or wireless transmission media (e.g., air and/or space).

There are several disadvantages of using timestamps or other generated reference signal to achieve synchronization of physiological signals. First, such an approach complicates the electronics of the sensor device measuring the signals because it requires some kind of an internal clock which must be initialized correctly using some external reference clock. This complexity also raises the cost associated with the additional resources. Second, this approach may lead to inaccurate synchronization if the internal clocks differ, which is occasionally caused by frequency drifts of the clock crystal in each sensor as a result of changing environmental or physical factors (e.g., temperature, stress, etc.).

Figure 1:
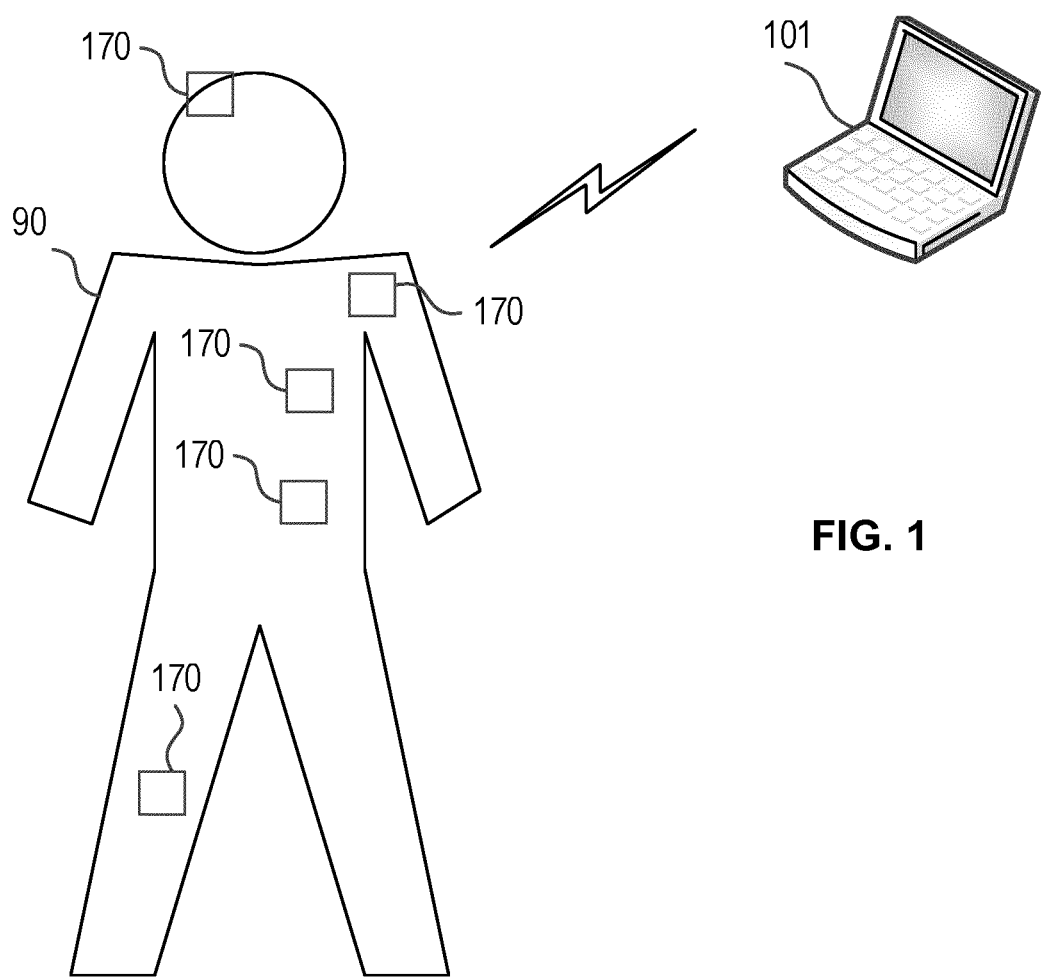
FIG. 1 illustrates an example physiological data collecting and analyzing environment.

FIG. 1 illustrates a physiological data collecting and analyzing environment in accordance with one or more examples described herein. In FIG. 1, one or more physiological sensors 170 may be connected to an individual 90. Physiological sensors 170 may include, for example, electrocardiogram (ECG), photoplethysmogram (PPG), and/or electroencephalogram (EEG) sensors configured to detect, record, or collect respiration, heartbeat, brain wave (e.g., beta, alpha, theta, delta, etc.), and gastrointestinal muscle movement signals (e.g., from the stomach, small intestine, etc.). Physiological sensors 170 may include other sensors for collecting other types of signals. As such, sensors 170 may be connected to various parts of the body associated with individual 90. For example, EEG sensors 170 may be in proximity to or in contact with the brain of individual 90 whereas ECG sensors 170 may be in proximity to or in contact with the heart of individual 90. The sensors shown are merely examples, and other types of sensors could also or alternatively be used.

Sensors 170 are configured to detect, collect, or record physiological signals associated with individual 90 and transmit these signals to computing platform 101. Transmission of physiological signals from sensors 170 to computing platform 101 may occur through any means, including a wireless or wired connection between sensors 170 and platform 101. In some implementations, physiological signals detected or collected by sensors 170 are stored in some storage. The stored physiological signals from the storage may be later transmitted to computing platform 101 for processing.

A physiological sensor 170 may detect, record, or collect one or more physiological signals or data, such as respiration, heartbeat, brain wave, and gastrointestinal muscle movement signals, etc. A physiological sensor 170 may also detect a composite physiological signal that include two or more physiological signal components, such as respiration, heartbeat, brain wave, and gastrointestinal muscle movement signal components, etc. In some aspects, a single physiological sensor 170 may detect, record or collect multiple types of physiological signal components, which may be separated, extracted, or filtered from the physiological signal recorded from or collected by the single physiological sensor 170. For example, a PPG sensor 170 may record PPG or heartbeat signal component and respiration signal component from individual 90. The physiological signal collected from sensor 170 may be processed by, for example, computing platform 101 to extract or filter a fast-moving heartbeat signal component and a slow-moving respiration signal component. As used herein, the term "fast-moving" signal or signal component is a relative term. This term means a signal or signal component that has a characteristic frequency higher than that of one or more other signals or signal components. Similarly, the term "slow-moving" signal or signal component is also a relative term. This term means a signal or signal component that has a characteristic frequency lower than that of one or more other signals or signal components.

Figure 2:
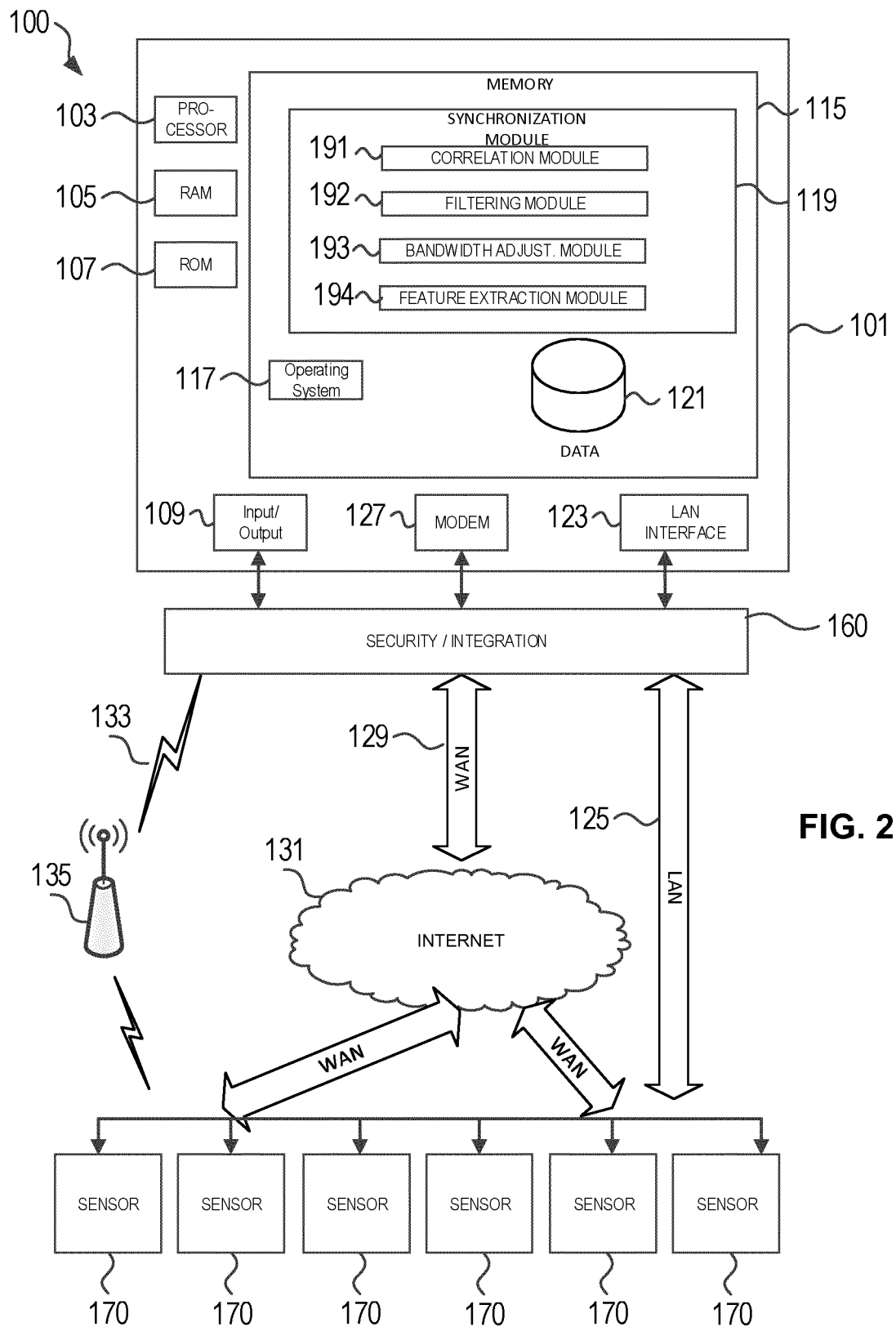
FIG. 2 illustrates an example computing and/or a network environment that may be used to implement features described herein.

FIG. 2 illustrates a block diagram of a computing platform 101 in a computer environment 100 that may be used in connection with one or more examples of the disclosure. Platform 101 may have one or more processors 103 for controlling overall operation of the platform 101 and its associated components, including RAM 105, ROM 107, input/output component 109, and memory 115. The platform 101, along with one or more additional platforms (e.g., sensors 170, security and integration hardware 160, etc.), may correspond to any of systems or devices, such as mobile computing devices, wearable computing devices, desktop computers, or computer servers, configured as described herein for processing, including synchronizing, one or more physiological signals collected directly or previously from sensors 170.

Input/Output (I/O) 109 may include a microphone, keypad, touch screen, and/or stylus through which a user of the computing platform 101 may provide input, and may also include one or more of a speaker for providing audio output and a video display device for providing textual, audiovisual and/or graphical output. Software may be stored within memory 115 and/or storage to provide instructions to processor 103 that when executed by processor 103, cause computing platform 101 to perform various actions such as, for example, actions described herein. For example, memory 115 may store software used by various components of computing platform 101, such as an operating system 117, synchronization module 119, and an associated internal database 121. The various hardware memory units in memory 115 may include volatile and nonvolatile, removable and non-removable media implemented in any method or technology for storage of information such as computer readable instructions, data structures, program modules or other data. Certain devices/systems within computing platform 101 may have minimum hardware requirements in order to support sufficient storage capacity, analysis capacity, network communication, etc. For instance, in some embodiments, one or more nonvolatile hardware memory units having a minimum size (e.g., at least 1 gigabyte (GB), 2 GB, 5 GB, etc.), and/or one or more volatile hardware memory units having a minimum size (e.g., 256 megabytes (MB), 512 MB, 1 GB, etc.) may be used in a computing platform 101 (e.g., a personal computing platform 101, a mobile computing platform 101, a wearable 101, a watch 101, a server 101, etc.), in order to store and execute a data synchronization software application, to collect and/or receive physiological signals from one or more sensors 170, to filter out signal components within predetermined frequency ranges, and to synchronize physiological signals from sensors 170 in communication with the same individual 90. Memory 115 also may include one or more physical persistent memory devices and/or one or more non-persistent memory devices. Memory 115 may include, but is not limited to, random access memory (RAM) 105, read only memory (ROM) 107, electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 103.

Processor 103 may include a single central processing unit (CPU), which may be a single-core or multi-core processor (e.g., dual-core, quad-core, etc.), or may include multiple CPUs. Processor(s) 103 may have various bit sizes (e.g., 16-bit, 32-bit, 64-bit, 96-bit, 128-bit, etc.) and various processor speeds (ranging from 100 MHz to 5 Ghz or faster). Processor(s) 103 and its associated components may allow computing platform 101 to execute a series of computer-readable instructions to, for example, filter out signal components from measured physiological data, to adjust the passband of any signal filtering operation performed by platform 101, to cross correlate two or more signals from different sensors 170, to extract various features of physiological signals measured from sensors 170, and to synchronize physiological signals, which may be further processed based on applications for the synchronized signals.

Platform 101 may operate in a networked computing environment 100 supporting connections to one or more remote devices, such as sensors 170 connected to individual 90. Sensors 170 may include some or all of the elements described above with respect to the computing platform 101. In addition, sensors 170 may include specialized software and hardware for collecting, storing, and processing physiological signals directly from individual 90. The network connections depicted in FIG. 1 include a local area network (LAN) 125, a wide area network (WAN) 129, and a wireless telecommunications network 133, but may also or alternatively include other networks. When used in a LAN networking environment, computing platform 101 may be connected to the LAN 125 through a network interface or adapter 123. When used in a WAN networking environment, computing platform 101 may include a modem 127 or other means for establishing communications over the WAN 129, such as network 131 (e.g., the Internet). When used in a wireless telecommunications network 133, platform 101 may include one or more transceivers, digital signal processors, and additional circuitry and software for communicating with wireless sensors 170 via one or more network devices 135 (e.g., base transceiver stations) in the wireless network 133.

Synchronization module 119 may be used by computing platform 101 to synchronize physiological signals from two or more sensors 170 using part of the signal data itself. To accomplish this functionality, synchronization module 119 may include one or more sub-modules, such as correlation module 191, filtering module 192, bandwidth adjustment module 193, and feature extraction module 194.

Synchronization module 119 may access physiological signal data stored in datastore 121 or residing in a cache associated with platform 101. As used herein, the term "signal data" refers to data representing signal or signals from one or more sensor 170. The data may have been measured from various physiological sensors, including PPG sensors attached to different parts of individual 90 (e.g., abdomen, chest, etc.), EEG sensors attached to the brain of individual 90, and other types of sensors configured to make other types of physiological measurements on individual 90 (e.g., gastrointestinal muscle movement measurements).

Accessed signal data from two or more sources may then be filtered using filtering module 192 to isolate a high frequency component of the collected signal, which may be live signal (e.g., real-time or substantially real-time signal) and/or stored signal (which has been recorded some time before and stored). In this aspect, the term "high frequency component" is a relative term. In particular, this term refers to any signal component having a higher frequency than one or more other components of the signal measured with sensors 170. The same signal component may be a low frequency component with respect to one or more signal components and a high frequency component with respect to another one or more signal components. To further explain, a respiration signal measured with PPG sensor 170 may include an embedded higher frequency heartbeat signal component (i.e., "fast-moving signal") within the lower frequency respiration signal (i.e., "slow-moving signal"). In this example, filtering module 192 may extract the high frequency (e.g., 0.75 to 2 Hz) heartbeat signal from the lower frequency (e.g., 0.15 to 0.5 Hz) respiration signal measured with PPG sensor 170.

As another example, EEG sensors 170 may measure signals reflecting brain activity. Filtering module 192 may be used to extract various types of brain signals from the measured data. For example, EEG signals may include beta brain waves, which occur within the 14 to 30 Hz frequency band, alpha brain waves, which occur within the 8 to 14 Hz frequency band, theta brain waves, which occur within the 4 to 8 Hz frequency band, delta brain waves, which occur within the 0.1 to 4 Hz frequency band, and gamma brain waves, which occur within the 30 to 50 Hz frequency band. Thus, a high frequency component of EEG signals measured by EEG sensor 170 and filtered by filtering module 192 may be alpha, theta, delta, or gamma brain waves if beta brain waves are also embedded in the measured EEG signal. Similarly, a high frequency component of EEG signals measured by EEG sensor 170 and filtered by filtering module 192 may be theta, delta, or gamma brain waves if alpha brain waves are also embedded in the measured EEG signal. In this way, any higher frequency component may be filtered from measured EEG signals that are composed of multiple types of brain waves.

Further still, sensors 170 may measure signals from gastrointestinal muscle movements, which occur at 0.05 Hz or in the 0.08 to 0.2 Hz range. Filtering module 192 may then be used to filter out embedded respiration signals, which occur within the 0.15 to 0.5 Hz band.

A bandwidth adjustment module 193 may be used to adjust the passband (i.e., frequency response) of the filter provided by filtering module 192 based on the characteristics of the input signal (i.e., the signal to be filtered). In particular, in some applications, bandwidth adjustment module 193 may be used to apply an adaptive filter by filtering module 192 to account for differences in the state or profile of an individual 90 whose physiological signals are being measured. For example, in a scenario where an embedded fast-moving heartbeat signal is being filtered out of a measured respiration signal, the embedded heartbeat signal may have a characteristic frequency closer to the upper part of the normal range (e.g., closer to 2 Hz) for an older individual 90 whereas a younger individual 90 may have a heartbeat signal with a characteristic frequency closer to the lower part of the normal range (e.g., closer to 0.75 Hz). Similarly, an individual 90 with a health condition (e.g., hypertension, diabetes, stress, fear, psychosis, etc.) may have an embedded heartbeat signal with a characteristic frequency that is different from an individual 90 without this condition. In yet a further example, if the heartrate information for an individual 90 is available from a first sensor or device 170 (e.g., smartwatch, ECG sensor, etc.), then that information may be used to adjust the filter characteristics of data collected from a second sensor or device 170 for the same or similar individual 90. Thus, bandwidth adjustment module 193 may be used to appropriately adjust the filtering properties of filtering module 192 and isolate the fast moving signal of interest.

Once filtered, separated, or extracted, the fast-moving signals from two different sensors may be cross-correlated using correlation module 191 to determine the relative delay between them so that the physiological signals (from different sensors) from which they were extracted can be synchronized. For example, correlation module 191 may perform a cross-correlation operation between the extracted fast-moving signals from two different sensors. The cross-correlation operation may result in an output with, for example, a maximum value or a minimum value at the point where the two physiological signals are aligned, thereby allowing computing platform 101 or another device to determine the time delay between the two physiological signals. Further, correlation module 191 may cross-correlate the higher frequency component of the measured signals (as opposed to lower frequency components) because the higher frequency component may have more pronounced features, such as peaks and troughs (i.e., higher frequency contents in the frequency domain) and may result in more accurate estimates or calculations of the relative delays between two or more physiological signals from different sensors.

Feature extraction module 194 may also be used to extract various features of the collected physiological signal data, such as the extrema (peaks and/or troughs of the signal), to improve the computational efficiency of signal quality validation from each sensor 170. For example, if the extracted features of the signal from a breathing sensor 170 do not contain peaks and troughs consistent with a breathing waveform, then the measured data may be omitted or rejected from the synchronization process. In this example, peaks and troughs of the measured waveform may be detected using any kind of time-based (using first and second order differences) or time-frequency-based (e.g., wavelet) methods.

Because the signal synchronization scheme discussed herein is passive and the signals to be synchronized may be embedded in the captured data, synchronization can be achieved even after the data is collected. Any error during data collection does not render the captured data unusable due to lack of synchronization. In contrast, in a time-stamp based method, metadata for achieving synchronization (e.g., calibration settings, sensor settings etc.) must be captured after the physiological signals have been collected. Thus, the signal synchronization approach discussed herein improves the efficiency of data collection. Moreover, the computational complexity of signal synchronization may be reduced using the approach discussed herein by matching time differences in the peaks and troughs of the captured signals in lieu of performing a full signal correlation.

Once features have been extracted from collected physiological signal data, the extracted features may be correlated (e.g., by the calculation of correlation coefficients) to aid in the signal synchronization process.

As used herein, the term "cross-correlation" of two or more signals refers to a measure of similarity of the signals as a function of the displacement of one relative to the other. Any measure of similarity can be used, including, for example, a sliding dot product or sliding inner-product. For example, the measure of similarity can be used for searching a long physiological signal for a shorter signal, a segment of a signal, or feature, such as known feature (e.g., a peak and trough).

As used herein, the term "correlation" between two or more signals refers more broadly to the dependence, association, connection, mutual relationship between the signals as determined by various techniques, including, for example, by the calculation of correlation coefficients and/or through the cross-correlation of the two signals.

Also illustrated in FIG. 2 is a security and integration layer 160, through which data may be sent and managed between computing platform 101 and remote devices such as sensors 170 and remote networks (125, 129, and 133). The security and integration layer 160 may comprise one or more separate computing devices, such as web servers, authentication servers, and/or various networking components (e.g., firewalls, routers, gateways, load balancers, etc.), having some or all of the elements described above with respect to the computing platform 101. As an example, a security and integration layer 160 of computing platform 101 may comprise a set of web application servers configured to use secure protocols and to insulate the platform 101 from sensors 170. In some cases, the security and integration layer 160 may correspond to a set of dedicated hardware and/or software operating at the same physical location and under the control of the same entities as computing platform 101. For example, layer 160 may correspond to one or more dedicated web servers and network hardware in an organizational datacenter or in a cloud infrastructure supporting a cloud-based signal processing system. In other examples, the security and integration layer 160 may correspond to separate hardware and software components which may be operated at a separate physical location and/or by a separate entity.

Although not shown in FIG. 2, various elements within memory 115 or other components in computing environment 100, may include one or more caches, for example, CPU caches used by the processing unit 103, page caches used by the operating system 117, disk caches of a hard drive, and/or database caches used to cache content from database 121. A CPU cache may be used by one or more processors in the processing unit 103 to reduce memory latency and access time. In such examples, a processor 103 may retrieve data from or write data to the CPU cache rather than reading/writing to memory 115, which may improve the speed of these operations. In some examples, a database cache may be created in which certain data from a database 121 (e.g., a database of stored physiological data captured from sensors 170, etc.) is cached in a separate smaller database on an application server separate from the database server. For instance, in a multi-tiered application, a database cache on an application server can reduce data retrieval and data manipulation time by not needing to communicate over a network with a back-end database server. These and/or other types of caches may be included in various embodiments, and may provide potential advantages in certain implementations. For example, these and/or other types of caches may provide as faster response times (e.g., for calculating the cross-correlations of two physiological signals) and less dependence on network conditions when transmitting and retrieving collected physiological data, associated patient data, etc., as well as receiving or transmitting software applications or application updates for synchronizing two or more sets of physiological data.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, and WiMAX, is presumed, and the various computer devices and system components described herein may be configured to communicate using any of these network protocols or technologies.

Figure 3:
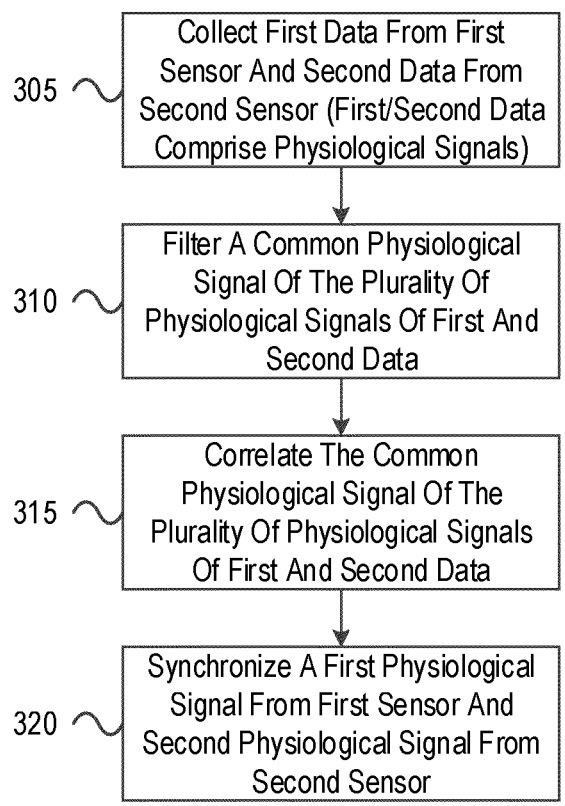
FIG. 3 is a flow chart illustrating an example method of synchronizing physiological data.

FIG. 3 is a flow chart illustrating one example method of synchronizing physiological data. Referring to FIG. 3, at step 305, the method may include the step of collecting first data from a first sensor and second data from a second sensor, each of the first data and the second data represents a plurality of physiological signal components. The first data and/or the second data may be collected directly from the first sensor and the second sensor (physiological signals detected and/or recorded by the first and second sensors), respectively. The first data and/or the second data may also be collected or retrieved from a storage (physiological signals detected and/or recorded previously by the first and second sensors, respectively). Subsequently, at step 310, the method may further include the step of extracting (e.g., by filtering or separating) a common physiological signal component of the first data and the second data. For example, the first data may include a heartbeat signal component and a respiration signal component. The second data may include a heartbeat signal component and a respiration component signal or other types of physiological signal components or physiological signals (e.g., heartbeat signal and one or more of respiration, brain wave (e.g., beta, alpha, theta, delta, etc.), and gastrointestinal muscle movement signals). In this example, the heartbeat signal component is a common physiological signal component of the first data and the second data. In other examples, the common physiological signal component may be another type of signal. In extracting or separating the higher-frequency common physiological signal component, the lower-frequency physiological signal components of the first and second data are also separated or isolated. Next, in step 315, the method may include correlating the common physiological signal component (e.g., heartbeat signal) of the plurality of physiological signal components of the first data and of the plurality of physiological signal components of the second data. Finally, in step 320, the method may include synchronizing a first physiological signal component (e.g., respiration signal component) including the first data from the first sensor and a second physiological signal component (e.g., respiration signal component or another type of physiological signal or signal component) including the second data from the second sensor based on the correlating. The process described above may be repeat, for example, at periodic intervals (e.g., every 10 minutes) to address, for example, the changing nature of unknown delays between two different physiological signals or two different sensors or types of sensors.

Figure 4A:
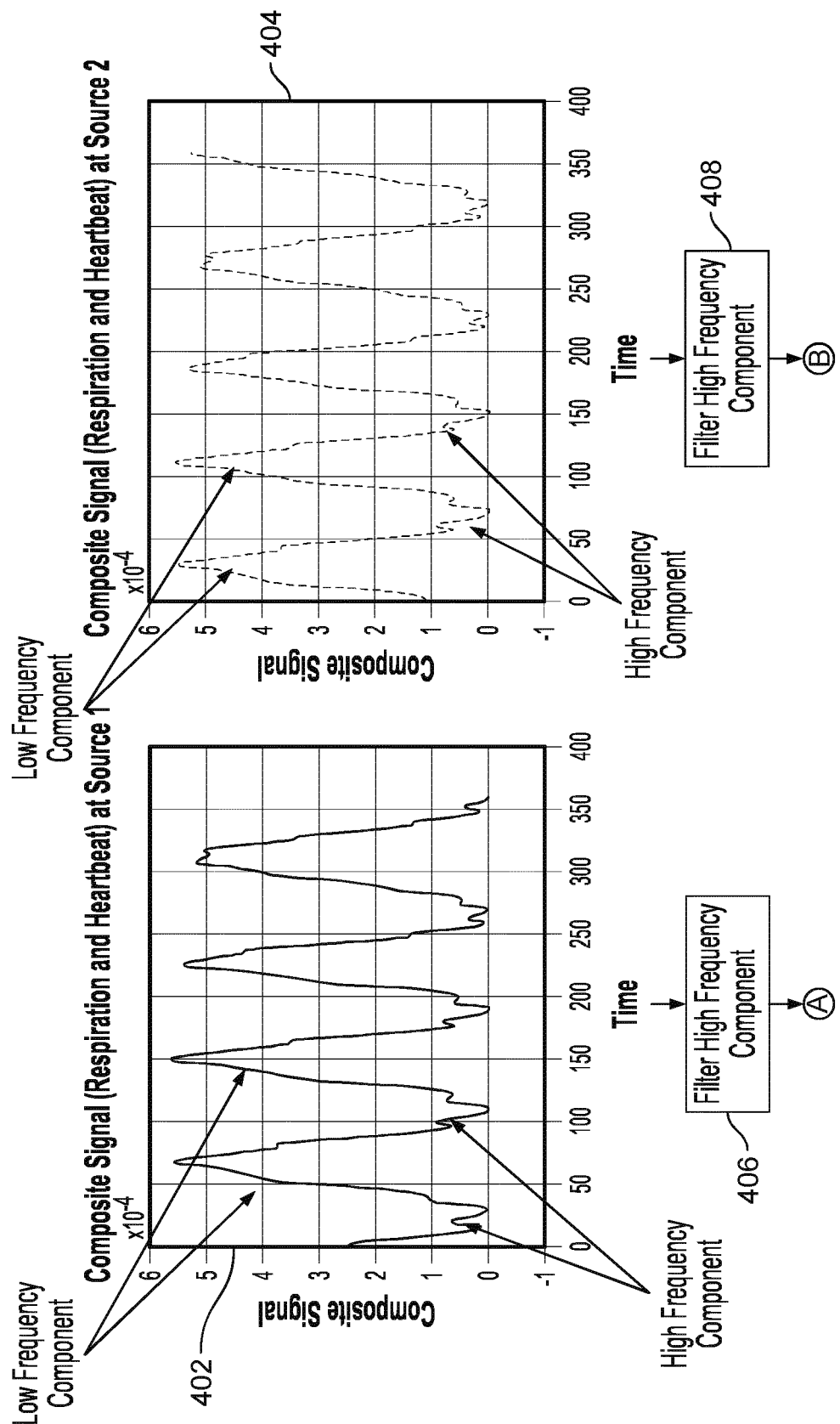
FIGS. 4A-4C depict an illustrative method for synchronizing physiological data in accordance with one or more example embodiments.
Figure 4B:
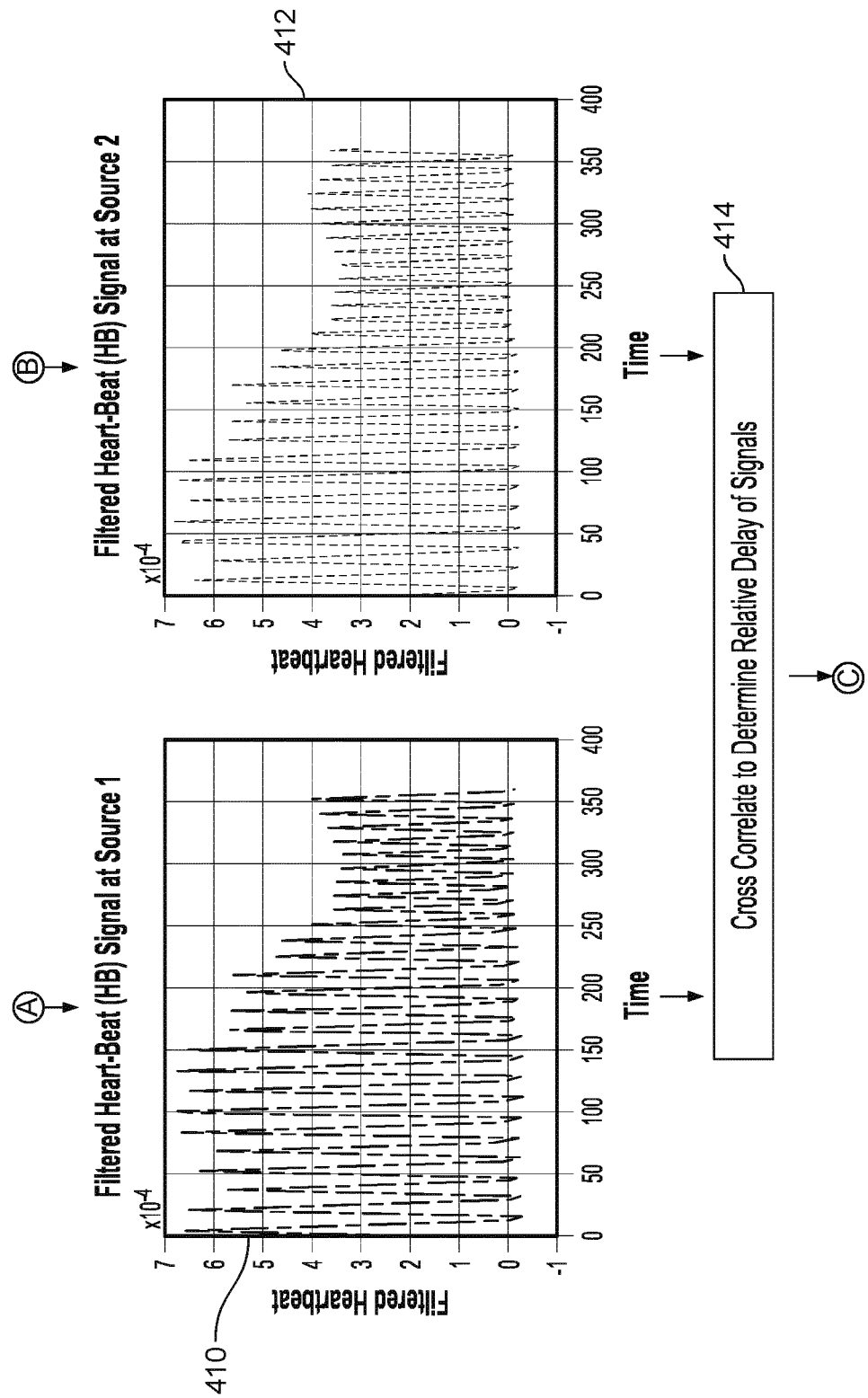
Figure 4C:
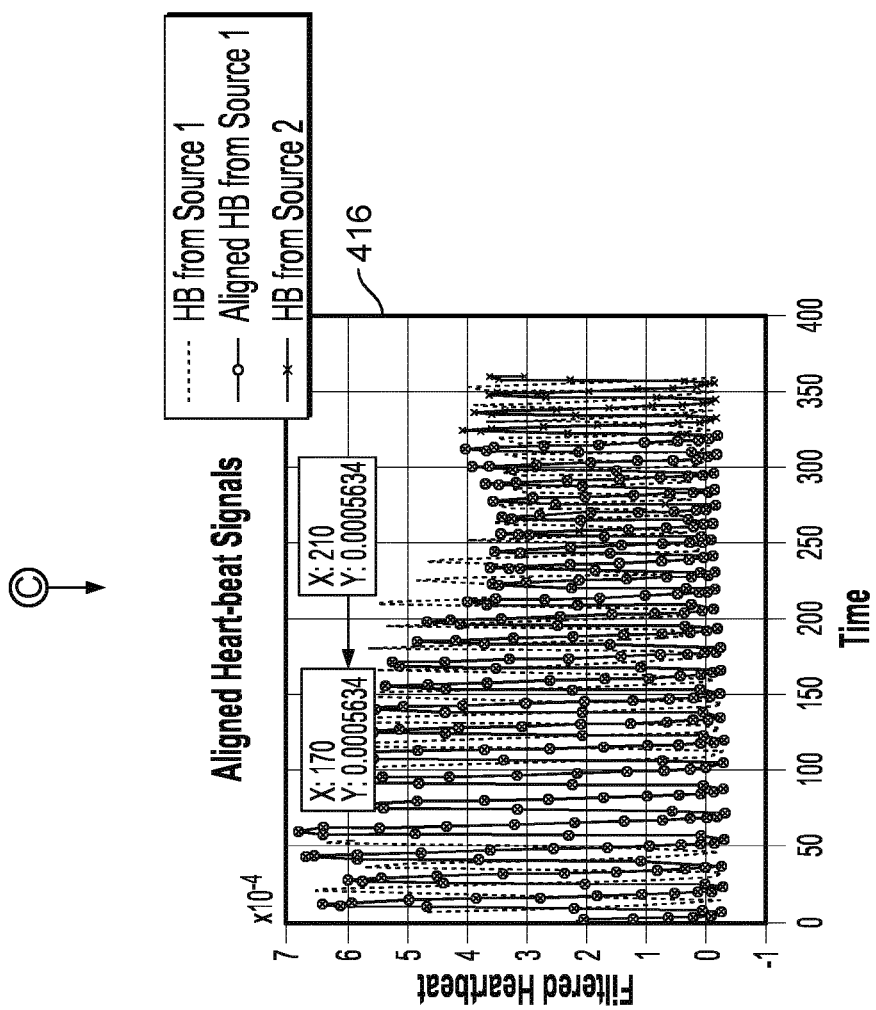

FIGS. 4A-4C show an example flow diagram of physiological signals being processed by computing platform 101. For this example, assume that two different PPG sensors 170 are attached to an individual 90. One of the sensors 170 is attached to the abdomen (e.g., source 1) of individual 90 and the other is attached to the chest (e.g., source 2) of individual 90. Assume also that each of the respiration signals captured by PPG sensors 170 has some unknown delay that can vary (e.g., based on the individual whose respiration is being measured, etc.) and cannot be estimated. Further assume that the delays will be different between the two sensors 170 due to differences in electronic latencies and other factors. These electronic latencies may be in the order of a few milliseconds to several seconds. In particular, sensors 170 may employ various techniques for signal conditioning, including observing a signal over a time interval via a buffer and producing a filtered output. In addition, even sensors 170 of the same type may have drifts associated with temperature, usage history etc. Different latencies can also result due to operator oversight (e.g., different settings being used at two identical sensors).

Now assume that graphs 402 and 404 of FIG. 4A depict measured physiological signals from the two PPG sensors 170, one attached to the abdomen and another attached to the chest of individual 90, respectively. As shown in FIG. 4A, the measured physiological signal from both sensors 170 includes both a low frequency component and an embedded high frequency component (e.g., the sensors 170 each detects and/or records the low frequency component and high frequency component as a composite signal). In this particular case, the low frequency component corresponds to a respiration signal and the high frequency component corresponds to a heartbeat signal. Filtering module 192 may be used to isolate the high frequency heartbeat component 406 and 408 from the composite signals 402 and 404, with the resulting isolated heartbeat signal from both sources shown in graphs 410 and 412 in FIG. 4B. In isolating the heartbeat signal, the lower-frequency signals, e.g., respiration signals, are may also be isolated. The heartbeat component or heartbeat signal may be used as a common physiological signal component or physiological signal for synchronizing the composite signals or the respiration signals from the abdomen and chest. A physiological signal component once extracted, isolated, separated may be referred as a physiological signal. The isolated heartbeat signals shown in graphs 410 and 412 may be cross-correlated 414 to determine the time delay between the two heartbeat signals extracted from two different sensors 170, as shown in graph 416 in FIG. 4C. The time delay between the two filtered heartbeat signals will be equivalent to the time delay between the measured respiration signals and, therefore, the time delay computed from the cross-correlation operation may be used to synchronize the measured composite signals or synchronize the respiration signals detected from the abdomen (e.g., source 1) and chest (e.g., source 2). As shown in graph 416, in this particular example, the time delay between the two filtered heartbeat signals is 40 time units and, therefore, to synchronize the measured respiration signals shown in graphs 402 and 404, the respiration signal shown in graph 402 must be time-shifted by 40 time units, for example, to the left.

Methods and systems discussed herein may be used for estimating volumetric breathing parameters in a more accessible and less cumbersome way. Conventional methods and systems for measuring breathing parameters involve the use of a spirometer. However, using a spirometer to perform continuous measurement of all breathing parameters (e.g., tidal volume, etc.) may not be practical for new health and fitness applications that benefit from data reflecting the full spectrum of breathing parameters because the spirometer is expensive (costs hundreds of dollars and hence is selectively accessible) and cumbersome (requires a mouth-pipe which is cumbersome for long-term use).

To accurately measure breathing parameters without a spirometer, an example set up may involve placing physiological sensors 170 on or near the chest and abdomen of an individual 90. Each location may measure breathing signals using one or more sensors 170 of the same or different types (e.g., from different sensor manufacturers). For example, the first sensor may capture chest movement (from breathing) and the second sensor may capture abdominal movement (from breathing). Moreover, the sensors 170 may use the same or different technologies. For example, sensor technologies in the form of easy-to-wear wearable chest-bands or contactless reflective technologies are two viable options. As described above, the captured breathing signals may be synchronized using a faster signal embedded in the captured breathing signals (e.g., a common heartbeat signal) from the same individual 90.

Signals to be synchronized may be different types of signals (e.g., a respiration signal and a gastrointestinal signal). In certain examples, the method described above may be used to synchronize two measured signals when the characteristic frequency of a common embedded signal (e.g., a heartbeat signal) is higher than the frequency ranges for the two measured signals (e.g., a respiration and gastrointestinal signal).

In some examples, computing platform 101 may correlate and synchronize more than two signals. In these examples, platform 101 may collect and access physiological signals from three or more physiological sensors 170. Accessed physiological signals (e.g., composite signals) may then be extracted, filtered, or otherwise isolated using filtering module 192 to isolate a common physiological signal component (e.g., a common high frequency component of each collected physiological signal). Platform 101 (e.g., via correlation module 191) may then correlate the common physiological signal from the three or more physiological sensors 170. To cross-correlate three or more signals, correlation module 191 may perform more than one cross-correlation. For example, to cross-correlate three signals, correlation module 191 may cross-correlate the first and second signals to determine a first optimal time delay between those two signals. Then correlation module 191 may cross-correlate the first and third signals to determine a second optimal time delay between those two signals. Finally, correlation module 191 may cross-correlate the second and third signals to determine a third optimal time delay between those two signals. Finally, based on these time delays, platform 101 may synchronize the signals from the three or more physiological sensors 170.

One or more features of the disclosure may be embodied in computer-usable data or computer-executable instructions, such as in one or more program modules, executed by processor(s) of one or more computers or other devices to perform the operations described herein. Generally, program modules include routines, programs, objects, components, data structures, and the like that perform particular tasks or implement particular abstract data types when executed by one or more processors in a computer or other data processing device. The computer-executable instructions may be stored as computer-readable instructions on a computer-readable medium such as a hard disk, optical disk, removable storage media, solid-state memory, RAM, and the like. The functionality of the program modules may be combined or distributed as desired in various embodiments. In addition, the functionality may be embodied in whole or in part in firmware or hardware equivalents, such as integrated circuits, application-specific integrated circuits (ASICs), field programmable gate arrays (FPGA), and the like. Particular data structures may be used to more effectively implement one or more aspects of the disclosure, and such data structures are contemplated to be within the scope of computer executable instructions and computer-usable data described herein.

Various aspects described herein may be embodied as a method, an apparatus, or as one or more computer-readable media storing computer-executable instructions. Accordingly, those aspects may take the form of an entirely hardware embodiment, an entirely software embodiment, an entirely firmware embodiment, or an embodiment combining software, hardware, and firmware aspects in any combination. In addition, various signals representing data or events as described herein may be transferred between a source and a destination in the form of light or electromagnetic waves traveling through signal-conducting media such as metal wires, optical fibers, or wireless transmission media (e.g., air or space). In general, the one or more computer-readable media may be one or more non-transitory and/or transitory computer-readable media.

As described herein, the various methods and acts may be operative across one or more computing servers and one or more networks. Functionality may be distributed in any manner, or may be located in a single computing device (e.g., a server, a client computer, and the like). For example, in alternative embodiments, one or more of the computing platforms or devices discussed above may be combined into a single computing platform or device, and the various functions of each computing platform or device may be performed by the single computing platform or device. In such arrangements, any and/or all of the above-discussed communications between computing platforms or devices may correspond to data being accessed, moved, modified, updated, and/or otherwise used by the single computing platform or device. Additionally or alternatively, one or more of the computing platforms or devices discussed above may be implemented in one or more virtual machines that are provided by one or more physical computing devices. In such arrangements, the various functions of each computing platform or device may be performed by the one or more virtual machines, and any and/or all of the above-discussed communications between computing platforms or devices may correspond to data being accessed, moved, modified, updated, and/or otherwise used by the one or more virtual machines.

Examples of the disclosure have been described herein. Numerous other examples, including modifications and variations within the scope and spirit of the appended claims, will occur to persons of ordinary skill in the art from a review of this disclosure. For example, one or more of the steps depicted in the illustrative figures may be performed in other than the recited order, and one or more depicted steps may be optional in accordance with aspects of the disclosure.

The invention claimed is:

1. An apparatus comprising
at least one processor; and
at least one non-transitory memory and computer program code;
the at least one memory and computer program code configured to, with the at least one processor, cause the apparatus at least to perform:
collecting first data from a first sensor and second data from a second sensor, wherein the first data represents a first plurality of physiological signal components and the second data represents a second plurality of physiological signal components, wherein the first data is at least partially different from the second data;
filtering the first data to isolate a high frequency signal component of the first data;
filtering the second data to isolate a high frequency signal component of the second data, comprising adjusting passband for the filtering based, at least partially, on information associated with the first data;
extracting a first physiological signal component of the first data and a second physiological signal component of the second data, wherein the first physiological signal component and the second physiological signal component comprise a common physiological signal component, wherein the first physiological signal component comprises a subset of the first plurality of physiological signal components comprising, at least, the high frequency signal component of the first data, wherein the second physiological signal component comprises a subset of the second plurality of physiological signal components comprising, at least, the high frequency signal component of the second data, wherein the first physiological signal component is extracted based, at least partially, on the filtering of the first data to isolate the high frequency signal component of the first data, wherein the second physiological signal component is extracted based, at least partially, on the filtering of the second data to isolate the high frequency signal component of the second data;
at a first point in time, correlating the first physiological signal component of the first plurality of physiological signal components of the first data and the second physiological signal component of the second plurality of physiological signal components of the second data;
based on the correlating, synchronizing a third physiological signal component included in the first data and a fourth physiological signal component included in the second data;
at a second point in time, repeating correlation of the first physiological signal component of the first plurality of physiological signal components of the first data and the second physiological signal component of the second plurality of physiological signal components of the second data, wherein the second point in time is a predefined interval after the first point in time; and
based on the repeated correlation, synchronizing the third physiological signal component included in the first data and the fourth physiological signal component included in the second data.

2. The apparatus of claim 1, wherein the first plurality of physiological signal components further comprises, at least, low frequency signal component, wherein the second plurality of physiological signal components further comprises, at least, a low frequency signal component, wherein adjusting the passband for the filtering comprises adjusting filtering properties of an adaptive filter.

3. The apparatus of claim 1, wherein the first sensor and the second sensor are configured to collect at least respiration signals.

4. The apparatus of claim 1, wherein the first sensor and the second sensor are configured to collect at least electroencephalogram signals.

5. The apparatus of claim 1, wherein the correlating comprises cross-correlating the first physiological signal component of the first data and the second physiological signal component of the second data.

6. The apparatus of claim 1, wherein the common physiological signal component of the first data and the second data corresponds to a heartbeat signal.

7. The apparatus of claim 1, wherein the common physiological signal component of the first data and the second data corresponds to at least one of gamma brain waves, beta brain waves, alpha brain waves, or theta brain waves.

8. The apparatus of claim 1, wherein at least one of the first sensor or the second sensor are configured to detect at least gastrointestinal muscle movement signals.

9. The apparatus of claim 1, wherein the first sensor and the second sensor are configured to detect signals of different types.

10. A method comprising:
collecting first data from a first sensor and second data from a second sensor, wherein the first data represents a first plurality of physiological signal components and the second data represents a second plurality of physiological signal components, wherein the first data is at least partially different from the second data;
filtering the first data to isolate a high frequency signal component of the first data;
filtering the second data to isolate a high frequency signal component of the second data, comprising adjusting a passband for the filtering based, at least partially, on information associated with the first data;
extracting a first physiological signal component of the first data and a second physiological signal component of the second data, wherein the first physiological signal component and the second physiological signal component comprise a common physiological signal component, wherein the first physiological signal component comprises a subset of the first plurality of physiological signal components comprising, at least, the high frequency signal component of the first data, wherein the second physiological signal component comprises a subset of the second plurality of physiological signal components comprising, at least, the high frequency signal component of the second data, wherein the first physiological signal component is extracted based, at least partially, on the filtering of the first data to isolate the high frequency signal component of the first data, wherein the second physiological signal component is extracted based, at least partially, on the filtering of the second data to isolate the high frequency signal component of the second data;

at a first point in time, correlating the first physiological signal component of the first plurality of physiological signal components of the first data and the second physiological signal component of the second plurality of physiological signal components of the second data;

based on the correlating, synchronizing a third physiological signal component included in the first data and a fourth physiological signal component included in the second data;

at a second point in time, repeating correlation of the first physiological signal component of the first plurality of physiological signal components of the first data and the second physiological signal component of the second plurality of physiological signal components of the second data, wherein the second point in time is a predefined interval after the first point in time; and based on the repeated correlation, synchronizing the third physiological signal component included in the first data and the fourth physiological signal component included in the second data.

11. The method of claim 10, wherein the first plurality of physiological signal components further comprises, at least, a low frequency signal component, wherein the second plurality of physiological signal components further comprises, at least, a low frequency signal component.

12. The method of claim 10, wherein the first sensor and the second sensor are configured to detect at least respiration signals.

13. The method of claim 10, wherein the first sensor and the second sensor are configured to collect at least electroencephalogram signals.

14. The method of claim 10, wherein the correlating comprises cross-correlating the first physiological signal component of the first data and the second physiological signal component of the second data.

15. The method of claim 10, wherein the common physiological signal component of the first data and the second data corresponds to a heartbeat signal.

16. The method of claim 10, wherein the common physiological signal component of the first data and the second data corresponds to at least one of gamma brain waves, beta brain waves, alpha brain waves, or theta brain waves.

17. The method of claim 10, wherein at least one of the first sensor or the second sensor are configured to detect at least gastrointestinal muscle movement signals.

18. The method of claim 10, wherein the first sensor and the second sensor are configured to detect signals of different types.

19. A non-transitory computer-readable media comprising program instructions stored thereon for performing at least the following:

collect first data from a first sensor and second data from a second sensor, wherein the first data represents a first plurality of physiological signal components and the second data represents a second plurality of physiological signal components, wherein the first data is at least partially different from the second data;

filter the first data to isolate a high frequency signal component of the first data;

filter the second data to isolate a high frequency signal component of the second data, comprising adjusting a passband for the filtering based, at least partially, on information associated with the first data;

extract a first physiological signal component of the first data and a second physiological signal component of the second data, wherein the first physiological signal component and the second physiological signal component comprise a common physiological signal component, wherein the first physiological signal component comprises a subset of the first plurality of physiological signal components comprising, at least, the high frequency signal component of the first data, wherein the second physiological signal component comprises a subset of the second plurality of physiological signal components comprising, at least, the high frequency signal component of the second data, wherein the first physiological signal component is extracted based, at least partially, on the filtering of the first data to isolate the high frequency signal component of the first data, wherein the second physiological signal component is extracted based, at least partially, on the filtering of the second data to isolate the high frequency signal component of the second data;

at a first point in time, correlate the first physiological signal component of the first plurality of physiological signal components of the first data and the second physiological signal component of the second plurality of physiological signal components of the second data;

based on the correlating, synchronize a third physiological signal component included in the first data and a fourth physiological signal component included in the second data;

at a second point in time, repeat correlation of the first physiological signal component of the first plurality of physiological signal components of the first data and the second physiological signal component of the second plurality of physiological signal components of the second data, wherein the second point in time is a predefined interval after the first point in time; and based on the repeated correlation, synchronize the third physiological signal component included in the first data and the fourth physiological signal component included in the second data.

20. The non-transitory computer-readable media comprising program instructions stored thereon of claim 19, wherein the common physiological signal component of the first data and the second data corresponds to a heartbeat signal.

* * * * *